(12) United States Patent
Tuneberg

(10) Patent No.: US 6,884,067 B2
(45) Date of Patent: Apr. 26, 2005

(54) ORTHODONTIC DEVICE FOR TREATMENT OF MALOCCLUSION

(75) Inventor: Lee H. Tuneberg, Sheboygan, WI (US)

(73) Assignee: American Orthodontics, Sheboygan, WI (US)

( * ) Notice: Subject to any disclaimer, the term of this patent is extended or adjusted under 35 U.S.C. 154(b) by 0 days.

(21) Appl. No.: 10/098,109

(22) Filed: Mar. 14, 2002

(65) Prior Publication Data

US 2002/0132207 A1 Sep. 19, 2002

Related U.S. Application Data

(60) Provisional application No. 60/275,814, filed on Mar. 14, 2001.

(51) Int. Cl.[7] ............................................... A61C 3/00
(52) U.S. Cl. ........................................................ 433/19
(58) Field of Search ............................................ 433/19

(56) References Cited

U.S. PATENT DOCUMENTS

| | | | |
|---|---|---|---|
| 3,997,970 A | 12/1976 | Hodgson | 433/20 |
| 4,462,800 A | 7/1984 | Jones | 433/19 |
| 4,551,095 A | 11/1985 | Mason | 433/19 |
| 4,708,646 A | 11/1987 | Jasper | 433/19 |
| 4,795,342 A | 1/1989 | Jones | 433/19 |
| 5,022,855 A | 6/1991 | Jeckel | 433/18 |
| 5,183,388 A | 2/1993 | Kumar | 433/19 |
| 5,352,116 A | 10/1994 | West | 433/19 |
| 5,435,721 A | 7/1995 | Vogt | 433/19 |
| 5,897,313 A | * 4/1999 | Cleary et al. | 433/19 |
| 6,053,730 A | * 4/2000 | Cleary | 433/19 |
| 6,328,562 B1 | 12/2001 | Sirney et al. | 433/19 |

* cited by examiner

Primary Examiner—John J Wilson
(74) Attorney, Agent, or Firm—Philip G. Meyers

(57) ABSTRACT

The invention provides a non-unitary jumper or connecting element that can utilize a thin strip as the jumper body while providing one or preferably both ends of the jumper with a reinforced end cap instead of a thin end flange that is subject to breakage. An orthodontic appliance of the invention includes a first attachment appliance attached to first teeth associated with a first jaw of a patient and a second attachment appliance attached to second teeth associated with a second jaw of the patient. A connecting element or jumper includes a generally flat, elongated, resilient strip configured for developing an axial pushing force from end to end when flexed between the first attachment appliance and the second attachment appliance for moving the first teeth relative to the second teeth. The strip has a pair of end portions. An end cap is mounted on one end portion of the strip and configured for attachment to an adjacent one of the first and second appliances, wherein the end cap has an end flange with an opening therethrough configured for bearing against the adjacent attachment appliance while allowing the connecting element to swivel relative to the adjacent attachment appliance. Suitable means are provided for mounting the other end of the connecting element to the other attachment appliance, such as a second end cap similar or identical to the first.

5 Claims, 3 Drawing Sheets

ORTHODONTIC DEVICE FOR TREATMENT OF MALOCCLUSION

This application claims priority of U.S. Provisional Patent Application Ser. No. 60/275,814, filed Mar. 14, 2001.

FIELD OF THE INVENTION

The present invention relates generally to orthodontic devices for treating malocclusions wherein a flexible element that exerts a small pushing force is mounting between attachment appliances attached to the upper and lower jaws of a patient.

BACKGROUND OF THE INVENTION

Orthodontic appliances known as "Class II" devices are designed to correct malocclusions between the upper and lower teeth without requiring patient cooperation, and for this purpose are mounted for continuous use and not easily removed by the patient. So-called Herbst appliances are well known for this purpose.

Jasper U.S. Pat. No. 4,708,646 discloses an elastic element or jumper, such as a spring surrounded by a rubber core, and having metal end caps for attachment to and between braces attached to the patient's upper and lower teeth. This device has proven highly successful in Class II treatment. The Jasper jumper uses end caps that can swivel at their points of attachment, providing greater patient comfort, but the number of components in the jumper, e.g. spring, cover and end caps, can cause occasional failure.

Vogt U.S. Pat. No. 5,435,721 describes an orthodontic appliance that performs in the same manner as a Jasper jumper, but wherein the jumper takes the form of a unitary, thin band of material (such as metal) that can be connected between the braces associated with the patient's upper and lower teeth. The connecting device has a body that is substantially flat and rectangular, with bent end portions that are preferably rounded for purposes of comfort. Each end portion includes an aperture for attachment to the braces associated with the patient's teeth. According to Vogt, at least one of the apertures of each connecting device is preferably keyed so that upon its attachment to the braces, swivelling of the connecting device is effectively precluded on the theory that this reduces breakage. However, although the Vogt device offers the simplicity of a unitary metal strip as the jumper, in practice the Vogt device has inadequate strength at its ends, which tear and fracture at the points of attachment. A need remains for a jumper that is more resistant to breakage, yet comfortable for the patient to wear and effective for orthodontic use.

SUMMARY OF THE INVENTION

The present invention provides a non-unitary jumper or connecting element that can utilize a thin strip as the jumper body while providing one or preferably both ends of the jumper with a reinforced end cap instead of a thin end flange that is subject to breakage. An orthodontic appliance according to the invention includes a first attachment appliance attached to first teeth associated with a first jaw of a patient and a second attachment appliance attached to second teeth associated with a second jaw of the patient, wherein the first appliance and the second appliance are capable of association with the teeth of the patient for applying forces to and between the first appliance and the second appliance and the teeth associated with the first appliance and the second appliance. A connecting element includes a generally flat, elongated, resilient strip configured for developing an axial pushing force from end to end when flexed between the first attachment appliance and the second attachment appliance for moving the first teeth relative to the second teeth. The strip has a pair of end portions. An end cap is mounted on one end portion of the strip and configured for attachment to an adjacent one of the first and second appliances, wherein the end cap has an end flange with an opening therethrough configured for bearing against the adjacent attachment appliance while allowing the connecting element to swivel relative to the adjacent attachment appliance. Suitable means are provided for mounting the other end of the connecting element to the other attachment appliance. Such means may be a second end cap similar or identical to the first, or may be of other types as discussed hereafter. The invention further provides an improved connecting element or jumper for use in a Class II appliance of the foregoing type, and also a set or kit for use by orthodontists to interchange end caps to create connecting elements in a variety of sizes as described further below.

According to another aspect of the invention, an orthodontic appliance includes first and second attachment appliances as described above but wherein at least one of the first and second appliances includes an outward projection (i.e., upright relative to the tooth surface, or in a buccal direction) ending in a stop. The connecting element has a pair of end portions, and suitable means are provided for mounting the ends of the connecting element to the attachment appliances, particularly to the arm or outward projection behind the stop, preferably in a manner that the strip is free to swivel at least vertically and slide along the arm. These and other aspects of the invention are discussed in the detailed description that follows.

BRIEF DESCRIPTION OF THE DRAWING

In the accompanying drawings, like numerals represent like elements except where section lines are indicated.

Figure 1:
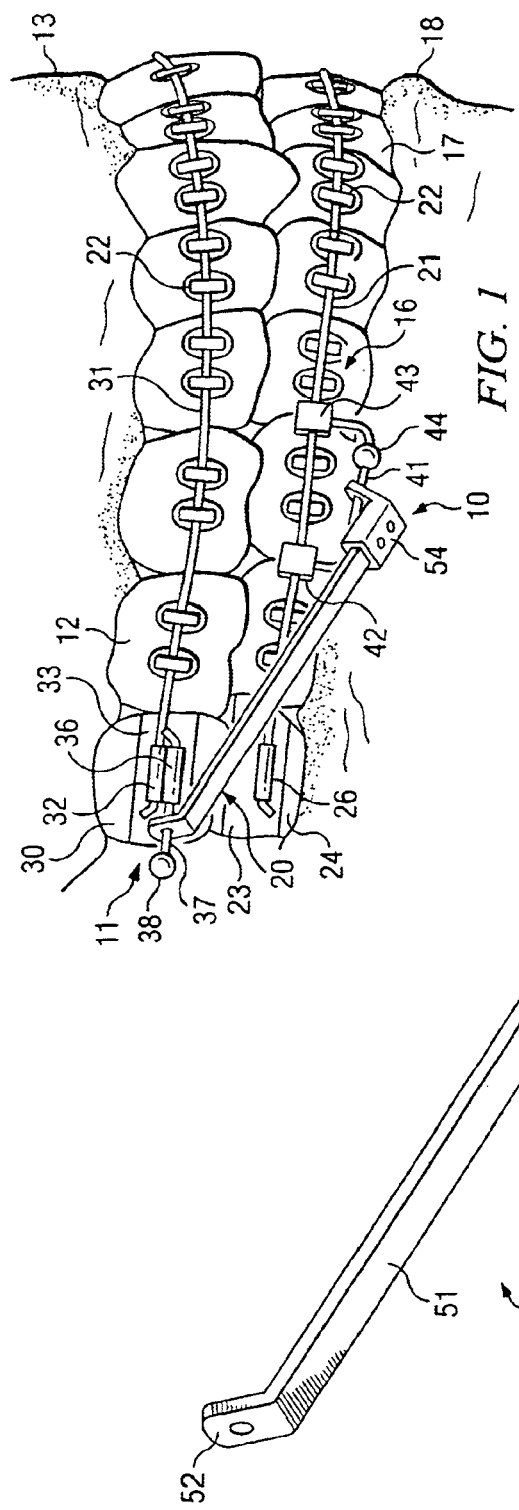
FIG. 1 is a side view of an orthodontic appliance of the invention installed in a patent's mouth.

While the making and using of various embodiments of the present invention are discussed in detail below, it should be appreciated that the present invention provides many applicable inventive concepts which can be embodied in a wide variety of specific contexts. The specific embodiments discussed herein are merely illustrative of specific ways to make and use the invention and are not to limit the scope of the invention.

DETAILED DESCRIPTION

Referring to FIGS. 1 to 4, an orthodontic appliance 10 of the invention includes a first (upper) attachment appliance 11 attached to upper teeth 12 associated with an upper jaw 13 of a patient, a second attachment appliance 16 attached to the lower teeth 17 associated with the lower jaw 18 of the patient, and a connecting element 20. These appliances are most commonly used in connection with conventional orthodontic braces mounted on the labial side of the teeth 12, 17, which braces include a lower arch wire 21 attached to mounting brackets 22 bonded to the patient's teeth. The ends of arch wire 21 on the lower jaw are retained by suitable means such as a orthodontic band 23 mounted on a molar 24 on each side. The end of the arch wire 21 on the lower jaw extends through a tube 26 on the outside of the band 23 and is bent at its outer end to hold it in place. An upper arch wire 31 on the teeth 12 of the upper jaw is retained in a similar manner at its ends by a tube 32 that is welded to a band 33 on a rear molar 30 of the patient's upper jaw, with the end of the upper arch wire 31 extending through the tubes 32.

First (upper) attachment appliance 11 includes band 33, a second tube 36 mounted next to tube 32, and a pin 37 ending in a ball stop 38. Pin 37 is bent at its front end and extends through tube 36 ending in ball 38. Connecting element 20 is mounted at one of its ends to pin 37 confined for sliding and/or swivelling movement between between ball 38 and tube 36. However, it should be emphasized that other orthodontic mounting systems known in the art could be used. For example, connecting element 20 could be mounted directly to the upper arch wire 31 between two brackets, and a stop can be provided on the arch wire to limit sliding of the connecting element. In this illustration, lower attachment appliance 16 includes a downwardly extending U-shaped wire 41 extending from two connectors 42, 43 on lower arch wire 21 and provided with a ball stop 44 to limit movement of the other end of connecting element 20. Each of these attachment appliances 11, 16 permit connecting element 20 to slide in a forward-back direction and also pivot, but neither of these types of movement are critical to the present invention, and thus one end of element 20 could be directly and rigidly secured to a bracket or band anchored to the desired tooth. A variety of attachment appliances are well known in the art as described in Jasper U.S. Pat. No. 4,708,646 and Vogt U.S. Pat. No. 5,435,721, the entire contents of which patents are incorporated herein by reference for all purposes.

Connecting element 20 is most preferably a generally flat, elongated, resilient strip 51 of metal (e.g., a nickel-titanium alloy) or plastic configured for developing an axial pushing force from end to end between first attachment appliance 11 and second attachment appliance 16 when flexed. Strip 51 may for example be configured as described in Vogt U.S. Pat. No. 5,435,721 incorporated by reference above. "Generally flat" in this context means at least about twice as wide as it is thick, as opposed to the solid flexible rod embodiments shown in the Jasper patent, which take up more space in the mouth and uses more material. Strip 51 has a pair of end portions 52, 53. An end cap 54 is mounted on end portion 53. First end 52, in this embodiment, is a bent end flange having a hole 56 therein to permit sliding movement along pin 37. Second end portion 53 is straight with a pair of spaced holes 56, 57 therein. Second end 53 is inserted into a close fitting slot 58 in the end of cap 54. Cap 54 also has a pair of through-holes 61, 62 which intersect slot 58 as shown and align with holes 56, 57 respectively. To complete the device, a pair of pins 63, 64 are inserted into holes 56, 61 and 57, 62 and secured in place, as by internal threads or preferably by laser welding. Cap 54 also has an end flange 66 having an hole 67 therein by which the other end of element 20 is mounted to wire 41. Prior to welding, it is preferred to coat either the inside of slot 58 or the outer surface of end portion 53 with a thin layer of a polymeric material (e.g., a rubber-based polymer such as Santoprene) effective for reducing adverse tribological effects.

The illustrated embodiment having the cap at the forward, lower jaw position is most preferred because the end cap has substantial size and will tend to interfere with the buccal tube at the rearward, upper jaw position. The size of through holes 52, 67 determines the extent to which element 20 can swivel and slide relative to the attachment appliances. Preferably these holes are large enough so that both ends can swivel freely, but embodiments wherein the device swivels only at hole 67, or where the device does not swivel at either end, are also within the scope of the invention.

Figure 5:
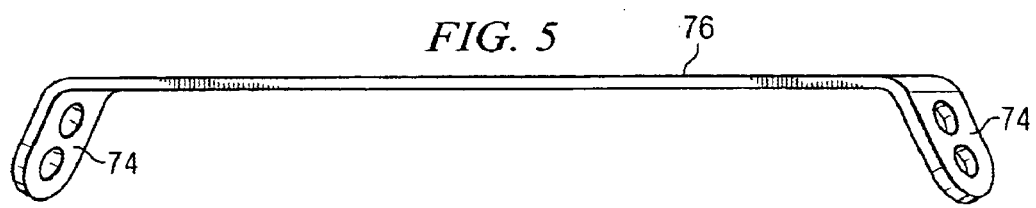
FIG. 5 is a side view of a first alternative embodiment of a strip according to the invention.
Figure 6:
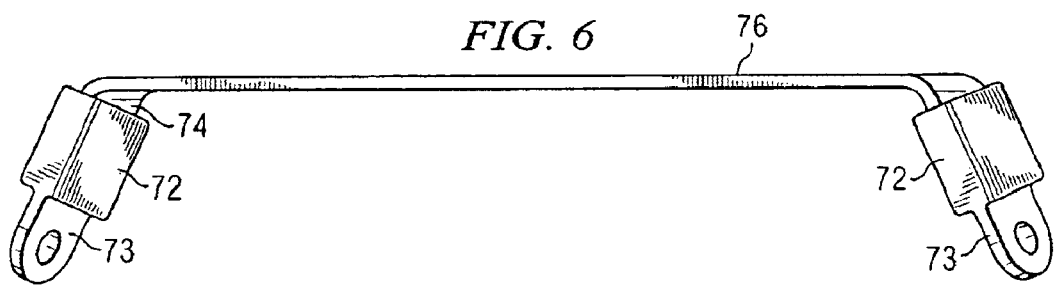
FIG. 6 is a side view of a connecting element using the strip shown in FIG. 5.
Figure 7:
FIG. 7 is a side view of a second alternative embodiment of a strip according to the invention, with an end cap in phantom.
Figure 8:
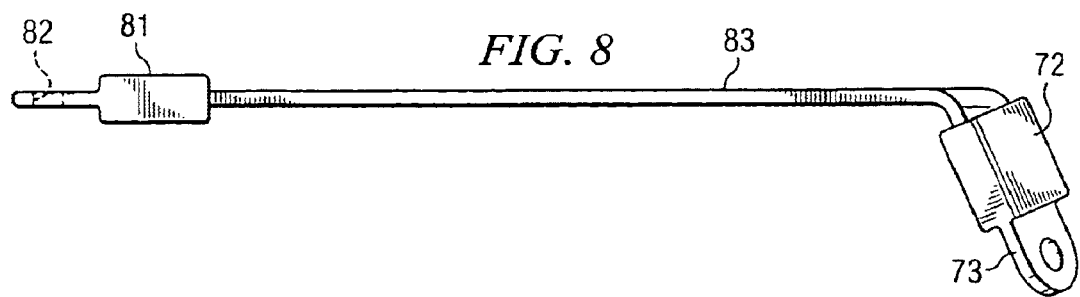
FIG. 8 is a side view of a third alternative connecting element.

In FIGS. 5 and 6, a second embodiment of a jumper or connecting element is shown wherein both ends are provided with an end cap 72 with a straight end flange 73. The bend is provided in the adjoining end portion 74 of the strip 76, rather than in the flange of the end cap 72. Thus, embodiments wherein both ends of the strip and/or cap are bent, both are straight, or one is bent and the other straight, are all within the scope of the invention. In another embodiment shown in FIG. 7, one end is the same as in FIGS. 5 and 6, whereas the other end comprises a bent end flange 77 only, with a single hole 78 therethrough that fits directly onto the wire of the mounting appliance. In FIG. 8, one end is the same as FIGS. 5 and 6, whereas the other end is mounted with a straight-flange cap 81 with a mounting hole 82 on a straight end portion of a strip 83. Cap 81 is essentially identical to cap 72 except that the flange projects straight out instead of at an acute angle relative to the lengthwise direction of the elongated strip.

Figure 2:
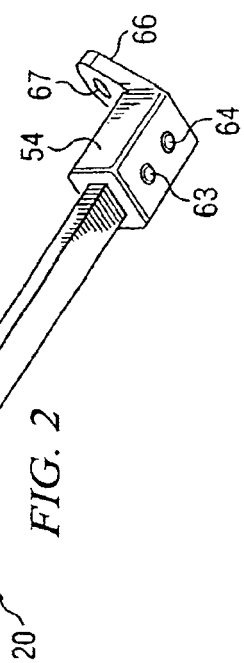
FIG. 2 is an enlarged side view of the connecting element used in FIG. 1.
Figure 3:
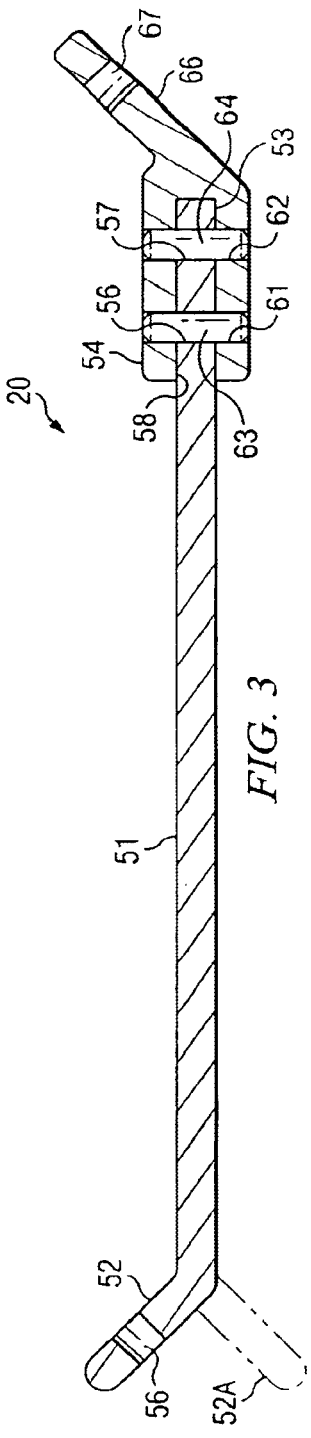
FIG. 3 is a lengthwise sectional view of the connecting element of FIG. 2.
Figure 4:
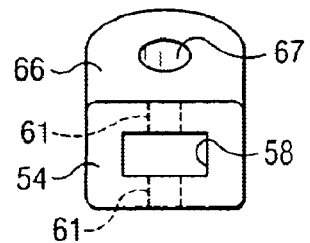
FIG. 4 is an end view of the end cap used in FIGS. 1–3.
Figure 9:
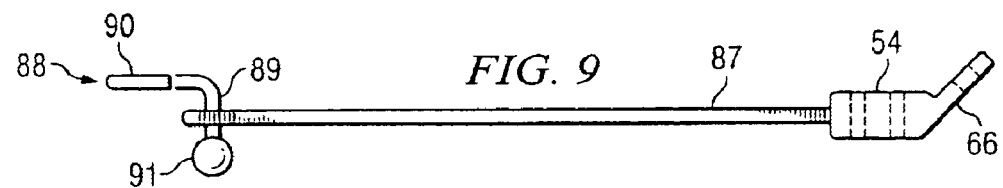
FIG. 9 is a top view of a fourth alternative embodiment of a connecting element, with an alternative mounting system according to the invention.
Figure 10:
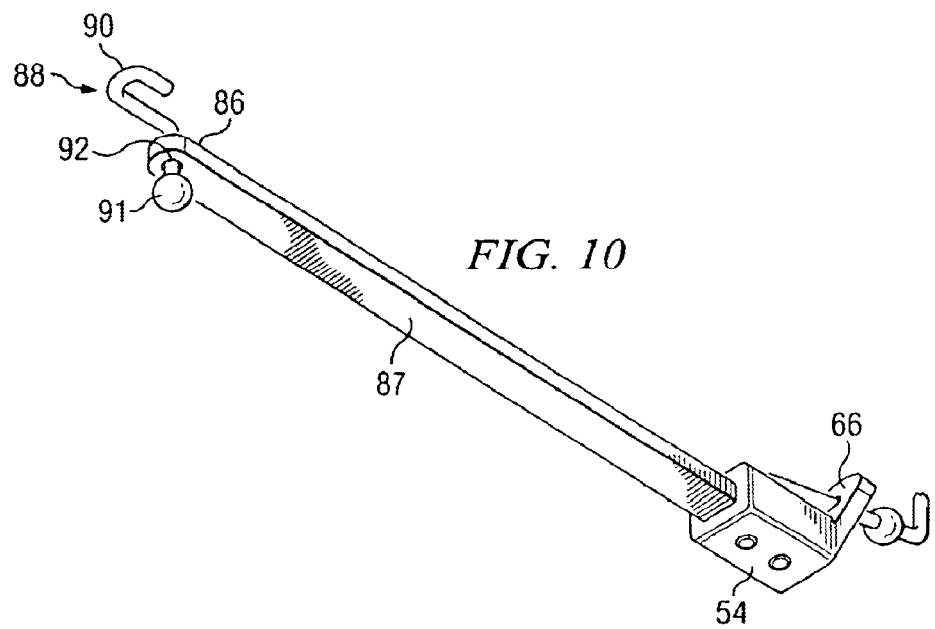
FIG. 10 is a perspective view of the embodiment shown in FIG. 9.

FIGS. 9 and 10 illustrate an alternative mounting system according to the invention wherein one end is provided with a cap 54 with an angled flange 66 as in FIG. 2, whereas the other end comprises a straight end portion 86 of the strip 87. In this embodiment, both ends of strip 87 are straight and strip 87 is completely flat with holes in its end portions as illustrated. A mounting wire 88 having an U-shaped segment 90 to be mounted in a buccal tube forms part of the upper attachment appliance. Wire 88 includes an arm 89 that extends outwardly from the upper teeth and ends in a ball 91. Strip 87 is mounted by a hole 92 in end portion 86 on arm 89, so that it can pivot on and slide along arm 89. This arrangement relieves stress on the strip at the upper point of attachment and provides for greater flexibility and patient comfort. As noted above, the capped end of the jumper is preferably at the front away from the buccal tube on the rear molar. However, an embodiment where both ends of the device have the configuration shown on the left side of FIGS. 9 and 10 is also within the scope of the invention. Such an alternative embodiment uses a flat strip with a single mounting hole at each end. In each of the foregoing embodiments, it will be understood that the flanges may be directed in the same or different directions as needed. For example, flange 52 can be directed in the opposite direction as shown in phantom lines as flange 52A.

The present invention further provides a kit or set which an orthodontist with welding equipment or the like can use to make jumpers in a variety of sizes. The kit contains a number of strips in any of the shapes discussed above, a number of end caps in any of the shapes described above, and a number of pins, screws or other fasteners for securing the caps onto the strips, preferably packaged in a common container with assembly instructions. The end caps come with end flanges of varying lengths in either the straight or bent styles, permitting the practitioner to custom make a jumper for a patient based on the size of the patient's mouth. In this manner a variety of sizes can be achieved using the same size of metallic strip, so that the strip manufacture can be standardized and only the end cap varies.

While certain embodiments of the invention have been illustrated for the purposes of this disclosure, numerous changes in the method and apparatus of the invention presented herein may be made by those skilled in the art, such changes being embodied within the scope and spirit of the present invention as defined in the appended claims.

What is claimed is:

1. A set for making connecting elements of in variable sizes, said connecting elements for use with a first attachment appliance attached to first teeth associated with a first jaw of a patient and a second attachment appliance attached to second teeth associated with a second jaw of the patient, wherein the first appliance and the second appliance are capable of association with the teeth of the patient for applying forces to and between the first appliance and the second appliance and the teeth associated with the first appliance and the second appliance, comprising:

a plurality of generally flat, elongated, resilient strips configured for developing an axial pushing force from end to end when flexed between the first attachment appliance and the second attachment appliance for moving the first teeth relative to the second teeth, each strip having a pair of end portions, wherein each strip has a mounting hole through the end portion by which it is to be connected to an end cap; and a plurality of end caps, configured for attachment to an adjacent one of the first and second appliances, wherein each end cap has an end flange with an opening therethrough configured for bearing against the adjacent attachment appliance while allowing the connecting element to swivel relative to the adjacent attachment appliance, and wherein each end cap has a mounting hole therein alignable with the mounting hole in one of the strips when the associated end portion of the strip is inserted into a slot in the end cap, and wherein the end flanges of the end caps are of varying lengths such that the opening through the end flange is in a variety of different positions relative to the strip.

2. The set of claim 1, further comprising a plurality of pins insertable into the aligned mounting holes for securing one of the caps to the one of the strips.

3. The set of claim 2, further comprising a common container for the strips, end caps and pins.

4. The set of claim 1 wherein the plurality of end caps include end caps with bent end flanges.

5. The set of claim 1 wherein the plurality of end caps include end caps with straight end flanges.

* * * * *